(12) United States Patent
Profendiner

(10) Patent No.: US 12,062,232 B2
(45) Date of Patent: Aug. 13, 2024

(54) VIEWING DIGITAL CONTENT IN A VEHICLE WITHOUT SUFFERING FROM MOTION SICKNESS

(71) Applicant: AUDI AG, Ingolstadt (DE)

(72) Inventor: Daniel Profendiner, Ingolstadt (DE)

(73) Assignee: AUDI AG, Ingolstadt (DE)

( * ) Notice: Subject to any disclaimer, the term of this patent is extended or adjusted under 35 U.S.C. 154(b) by 49 days.

(21) Appl. No.: 16/652,639

(22) PCT Filed: Sep. 20, 2018

(86) PCT No.: PCT/EP2018/075497
§ 371 (c)(1),
(2) Date: Mar. 31, 2020

(87) PCT Pub. No.: WO2019/068477
PCT Pub. Date: Apr. 11, 2019

(65) Prior Publication Data
US 2020/0242361 A1 Jul. 30, 2020

(30) Foreign Application Priority Data
Oct. 4, 2017 (DE) ..................... 10 2017 217 592.3

(51) Int. Cl.
*G06F 1/16* (2006.01)
*G06V 20/20* (2022.01)
*H04W 4/40* (2018.01)
*H04W 4/80* (2018.01)

(52) U.S. Cl.
CPC .............. *G06V 20/20* (2022.01); *G06F 1/163* (2013.01); *H04W 4/40* (2018.02); *H04W 4/80* (2018.02)

(58) Field of Classification Search
CPC ...... H04W 4/40; H04W 4/80; G06K 9/00791; G06B 2027/0183
See application file for complete search history.

(56) References Cited

U.S. PATENT DOCUMENTS

| 9,459,692 B1 | 10/2016 | Li |
| 2006/0015000 A1 | 1/2006 | Kim |
| 2012/0289767 A1 | 11/2012 | Yeh |
| 2014/0152792 A1* | 6/2014 | Krueger ............... A61B 5/4863 348/78 |

(Continued)

FOREIGN PATENT DOCUMENTS

| CN | 104977717 A | 10/2015 |
| CN | 106056973 A | 10/2016 |

(Continued)

OTHER PUBLICATIONS

McGill et al., "I Am the Passenger: How Visual Motion Cues Can Influence Sickness for In-Car VR" (Year: 2017).*

(Continued)

*Primary Examiner* — Hilina K Demeter
(74) *Attorney, Agent, or Firm* — STAAS & HALSEY LLP

(57) ABSTRACT

Digital content can be viewed in a vehicle without suffering from motion sickness by use of a system which includes a vehicle and data glasses. The vehicle includes a control unit and a plurality of sensors connected to the control unit. The data glasses can be wirelessly connected to the control unit and are intended to display a virtual 3-D integrating the digital content.

20 Claims, 1 Drawing Sheet

(56) References Cited

U.S. PATENT DOCUMENTS

| | | |
|---|---|---|
| 2014/0362113 A1 | 12/2014 | Benson et al. |
| 2015/0097860 A1 | 4/2015 | Alaniz et al. |
| 2015/0100179 A1* | 4/2015 | Alaniz .................. G06F 3/011 |
| | | 701/1 |
| 2015/0294505 A1 | 10/2015 | Atsmon |
| 2016/0042543 A1 | 2/2016 | Hashimoto et al. |
| 2016/0042566 A1* | 2/2016 | Mao ...................... A63F 13/67 |
| | | 463/32 |
| 2016/0167672 A1* | 6/2016 | Krueger ................ G16H 40/63 |
| | | 340/576 |
| 2016/0238852 A1 | 8/2016 | Ellsworth et al. |
| 2017/0076502 A1 | 3/2017 | Chen et al. |
| 2017/0227765 A1 | 8/2017 | Mammou et al. |
| 2017/0251176 A1 | 8/2017 | Smolyanskiy et al. |
| 2017/0254659 A1 | 9/2017 | Fukumoto |
| 2017/0372150 A1* | 12/2017 | Mayser ...................... G06T 7/13 |
| 2018/0081426 A1* | 3/2018 | Rothkopf ................ G06F 3/012 |
| 2018/0089900 A1* | 3/2018 | Rober ...................... B60Q 9/00 |
| 2018/0165942 A1 | 6/2018 | Hoshino |
| 2018/0357836 A1 | 12/2018 | Ishiguro et al. |
| 2019/0041228 A1* | 2/2019 | Singhal ................ G05D 1/0088 |

FOREIGN PATENT DOCUMENTS

| | | |
|---|---|---|
| DE | 101 56 219 C1 | 8/2003 |
| DE | 10 2013 021 137 A1 | 6/2015 |
| DE | 11 2014 001 764 | 12/2015 |
| DE | 10 2014 213 021 A1 | 1/2016 |
| DE | 10 2014 019 579 A1 | 6/2016 |
| DE | 10 2015 004 749 A1 | 10/2016 |
| DE | 10 2015 011 616 A1 | 3/2017 |
| DE | 10 2017 217 592.3 | 10/2017 |
| EP | 2 100 773 A1 | 9/2009 |
| EP | 2 933 707 | 10/2015 |
| EP | 3 316 571 | 5/2018 |
| JP | 2014-200018 | 10/2014 |
| JP | 2015-204616 | 11/2015 |
| JP | 2017-1634 | 1/2017 |
| JP | 2017-146963 | 8/2017 |
| WO | 2016/208546 | 12/2016 |
| WO | PCT/EP2018/075497 | 9/2018 |

OTHER PUBLICATIONS

Chinese Office Action dated May 31, 2021, in Chinese Patent Application No. 201880064145.4.
English Translation of International Preliminary Report on Patentability for PCT/EP2018/075497, dated Nov. 19, 2019, 12 pages.
English Translation of Japanese Office Action dated Apr. 20, 2021 in Japanese Patent Application No. 2020-519436, 4 pages.
Metz: "Oculus Founder Palamer Luckey on What It Will Take to Make Virtual Reality Really Big", Mar. 17, 2016, 2 pages.
Sauter: "Qualcomm zeigt Referenz-VR-Headset ohne Smartphone", Sep. 6, 2016, 1 page.
German Office Action dated Jul. 27, 2018 from German Application No. 10 2017 217 592.3, 5 pages.
Hock et al., "CarVR: Enabling In-Car Virtual Reality Entertainment", 11 pages.
"Beyond Reality: Head-Mounted Displays for Mobile Systems Researchers", GETMOBILE: Mobile Computing and Communications, ACM, vol. 21, Issue 2, Jun. 2017, pp. 9-15.
"In-Car use of VR HMDs by passengers," Multimodal Interaction Group HCI Research at the University of Glasgow, Glasgow Interactive Systems Group, available at http://mig.dcs.gla.ac.uk/in-car-use-of-vr-hmds-by-passengers/ (2017).
International Search Report dated Dec. 17, 2018 from International Application No. PCT/EP2018/075497, 10 pages.
Korean Office Action from Korean Application No. 10-2020-7011994 dated Aug. 31, 2021 ( including translation.

* cited by examiner

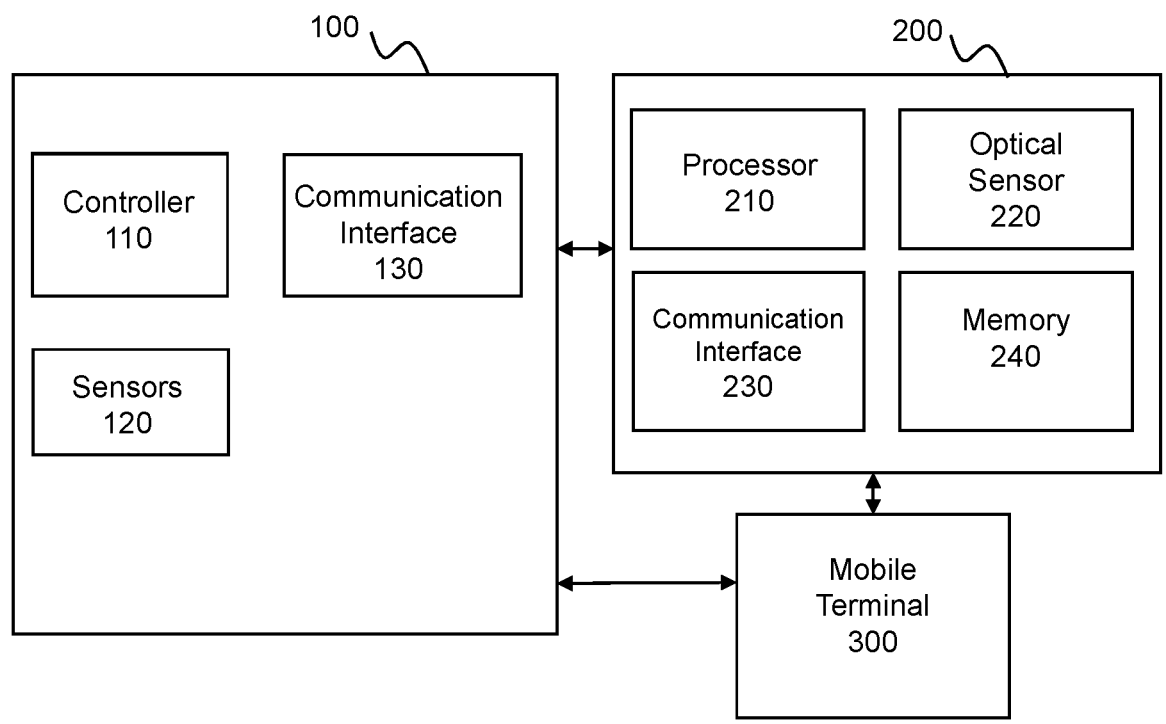

VIEWING DIGITAL CONTENT IN A VEHICLE WITHOUT SUFFERING FROM MOTION SICKNESS

CROSS REFERENCE TO RELATED APPLICATIONS

This application is a U.S. national stage of International Application No. PCT/EP2018/075497 filed on Sep. 20, 2018. The International Application claims the priority benefit of German Application No. 10 2017 217 592.3 filed on Oct. 4, 2017. Both International Application No. PCT/EP2018/075497 and German Application No. 10 2017 217 592.3 are incorporated by reference herein in their entirety.

BACKGROUND

Described herein is a system for viewing digital content in a vehicle without suffering from motion sickness, which system includes a vehicle having a control unit and a plurality of sensors connected to the control unit and data glasses (e.g., Head Mounted Device, HMD) which can be wirelessly connected to the control unit and are intended to display a virtual 3-D scene integrating the digital content.

The occupants of a vehicle are exposed to different accelerations during a journey. The accelerations include, on the one hand, linear accelerations (longitudinal accelerations) of the vehicle which act in a direction of travel of the vehicle and are caused by accelerating or braking. On the other hand, the occupants experience rotational accelerations (lateral accelerations) which, depending on the spatial orientation of an axis of rotation based on the direction of travel of the vehicle, are referred to as pitching (axis of rotation horizontal and perpendicular to the direction of travel), rolling (axis of rotation parallel to the direction of travel) or yaw (axis of rotation vertical and perpendicular to the direction of travel). Rotational accelerations are caused directly by steering and by the topology of the ground and indirectly as a resilient response to all of the above-mentioned direct accelerations.

An occupant of a vehicle can suffer from dizziness, headache, heart rate increase, nausea or vomiting (motion sickness) during a journey in the vehicle if the visual perception of position, orientation and acceleration, which is conveyed to the occupant via the eyes (sense of sight), is not consistent with the perception of the same variables which is conveyed via the vestibular system (sense of balance).

Such a discrepancy can occur, for example, in an occupant in the vehicle who is reading a book during the journey or is viewing digital content on a mobile terminal such as a smartphone or a tablet. In this case, the occupant, with his gaze lowered, focuses on a page of a book which is kept as still as possible or a display of a mobile terminal which is kept as still as possible, while his sense of balance is continuously stimulated by journey-related accelerations of the vehicle. However, an occupant who is neither reading a book nor viewing a display of a mobile terminal, but whose visual perception of an environment of the vehicle is restricted or impeded—for example the clear view to the front of an occupant sitting in the rear of the vehicle is partially blocked by front vehicle seats and headrests—can be affected by motion sickness.

U.S. Patent Application Publication No. 2006/0015000 A1 describes a system, a method and an apparatus for a vehicle for protecting rear-seat occupants of the vehicle from motion sickness. The system includes a forward-facing external camera and a display unit which is fitted to a rear side of a front headrest of the vehicle and is arranged in the field of view of a rear-seat occupant. The display unit makes a video stream recorded by the external camera continuously visible to the occupant. In this case, the environment in front of the vehicle which is recorded by the external camera is always directly dependent on the spatial position and orientation of the vehicle and thus reflects all accelerations occurring during the journey in real time, with the result that the risk of motion sickness is reduced or eliminated for the rear-seat occupant. The video stream can also be used as the background of static text presented in the foreground by the display unit. The rear-seat occupant can then read the text at the same time and can receive visual stimuli which are consistent with the vestibular perceptions of acceleration.

However, with this solution, the viewing direction of the rear-seat occupant is predefined by the position of the display unit. In contrast to a book which is usually read with the head inclined, the reading takes place with a gaze directed straight ahead, as a result of which the occupant can be easily distracted by stimuli from the vehicle or an environment of the vehicle. The solution is also primarily suitable for rear-seat occupants since it is difficult to appropriately fit the display unit for a front-seat occupant. However, this disadvantage can be avoided.

For example, U.S. Patent Application Publication No. 2016/238852 A1 and U.S. Patent Application Publication No. 2017/227765 A1 each describe data glasses (Head Mounted Display, HMD) which are suitable as a display unit in a vehicle.

German Patent Application No. 10 2014 019 579 A1 thus describes a system for operating a display unit in a vehicle. The display unit may be in the form of data glasses and can make text visible for reading to an occupant of the vehicle wearing the data glasses. The vehicle has a plurality of sensors for capturing movement information relating to the vehicle. The display unit is configured to receive the movement information and to display a decentralized background for the text which is calculated, on the basis of the received movement information, in real time in a manner consistent with the accelerations of the vehicle. In this manner, a risk of motion sickness is reduced for the wearer of the data glasses when reading the text.

Similar systems are described in U.S. Patent Application Publication No. 2014/362113 A1, German Patent Application No. 10 2014 019579, and German Patent Application No. 101 56 219 C1.

In contrast, German Patent Application No. 101 56 219 C1 describes a method for reducing motion sickness when viewing moving images in a vehicle. An apparatus suitable for the method includes a display unit (Head Mounted Device, HMD) which is fitted to the head of an occupant and has six acceleration sensors, a position/orientation sensor (Six Degrees Of Freedom, 6DOF Tracker) and an optional mini camera. The display unit is coupled to a computer arranged separately from the display unit in the vehicle in a wireless or wired manner. The computer is configured to play back data from a DVD (Digital Versatile Disc), a video, a VR application (Virtual Reality) or an AR application (Augmented Reality), to computationally transform the data on the basis of signals from the sensors of the display unit and to output the data to the display unit in such a manner that the visual perception of the wearer of the display unit is consistent with his vestibular perception.

This method requires a high bandwidth for transmitting the moving image streams from the computer to the display unit. If the display unit is coupled to the computer in a wired manner, a sufficient bandwidth can be achieved without any problems. However, this variant is associated with difficult handling of the display unit on account of the cable. In contrast, there is simple handling without any problems in the case of the wireless coupling, whereas a sufficient bandwidth cannot always be ensured when transmitting the moving image streams in the case of high resolution and a high image change rate. This problem is intensified if a plurality of occupants of the vehicle each use a display unit at the same and are looking at different moving image streams.

SUMMARY

The system described herein is therefore based on providing an improved system for reducing motion sickness when viewing digital content in a vehicle, which system is easy for the occupants to handle and manages with a low bandwidth. In addition, the disclosure is to specify an improved method for displaying digital content in a vehicle.

One subject matter of the disclosure is a system for viewing digital content in a vehicle without suffering from motion sickness. The system includes a vehicle having a control unit and a plurality of sensors connected to the control unit, and data glasses which can be wirelessly connected to the control unit and are intended to display a virtual 3-D scene integrating the digital content.

According to the disclosure, the control unit of the vehicle is configured to calculate control variables from sensor data received from the sensors and to transmit the control variables to the data glasses. The control unit therefore preprocesses the sensor data by calculating control variables for the data glasses therefrom. The preprocessing of the sensor data by the control unit can reduce the data volume to be transmitted if fewer control variables are required than sensor data are received. A further reduction can be achieved if the frequency of the control variable calculation is selected to be lower than the frequency of the sensor data reception.

Accordingly, according to the disclosure, the data glasses are configured to receive the control variables and to calculate the virtual 3-D scene (Virtual Reality, VR) on the basis of the received control variables. A virtual 3-D scene usually requires a large data volume for its display. If a virtual 3-D scene is intended to counteract motion sickness, this data volume must be calculated in real time in a manner consistent with the accelerations of the vehicle and displayed in the data glasses. The disclosure is based on the consideration of configuring the data glasses to calculate a virtual 3-D scene on the basis of control variables. In this manner, no data-intensive virtual 3-D scenes need to be transmitted to the data glasses in order to display the scenes in the data glasses. Rather, it is sufficient to transmit a few control variables relevant to the calculation, for which purpose a considerably lower bandwidth is required.

In one embodiment, the vehicle and the data glasses each have wireless communication interfaces which are complementary to one another, for example IR interfaces, Bluetooth interfaces, WiFi interfaces and/or NFC interfaces. Known or future communication interfaces which differ from the communication interfaces mentioned are within the scope of protection of the disclosure. It goes without saying that the vehicle and the data glasses may also have a plurality of complementary interface pairs from which the wearer of the data glasses can select any desired interface pair in order to connect the data glasses to the vehicle.

In one example embodiment, the control variables calculated by the control unit include an absolute position, an angle with respect to the horizon, a lateral acceleration and a longitudinal acceleration of the vehicle, and/or the data glasses are configured to post-process, for example smooth, the received control variables before calculating a virtual 3-D scene. In other words, four control variables are sufficient to calculate virtual 3-D scenes in a manner consistent with the accelerations of the vehicle. The absolute position of the vehicle can be used for spatial arrangement inside the virtual 3-D scene. On the basis of the angle with respect to the horizon, the perspective of the wearer of the data glasses with respect to the virtual 3-D scene can be simulated in a manner corresponding to a real viewing direction. The longitudinal and lateral accelerations are the most important control variables for reducing the risk of motion sickness. They can be used to accelerate the virtual 3-D scene in a manner consistent with the vehicle, as a result of which a discrepancy between the visual perception and the vestibular perception can be reduced or avoided.

In a further embodiment, the system includes a mobile terminal which can be wirelessly connected to the vehicle and/or to the data glasses and is intended to display vehicle parameters and/or journey parameters, for example a smartwatch, and the data glasses are configured to integrate a virtual terminal corresponding to the mobile terminal into a calculated virtual 3-D scene, with the result that the vehicle parameters and/or journey parameters displayed by the mobile terminal are visible on the virtual terminal. The simultaneous use of a mobile terminal and its virtual equivalent creates a consistent interactive experience for the wearer of the data glasses which overcomes the boundary between the real world and the virtual world. A smartwatch is particularly suitable for this purpose because the wearer continuously wears it on a wrist and its use is very comfortable.

In one embodiment, the data glasses are configured to integrate a visual indication, for example an indication using imagery, for a wearer of the data glasses, for example a driver of the vehicle, into the calculated virtual 3-D scene in order to request the wearer of the data glasses to remove the data glasses. For example, the calculated virtual 3-D scene can include a portal which is virtually passed through when the wearer is intended to remove the data glasses. This enables a very natural interactive experience for the wearer of the data glasses.

In a further embodiment, the data glasses include at least one optical sensor, for example a camera, for capturing an environment of the data glasses and a digital model of an interior environment of the vehicle, and the data glasses are configured to use the digital model to distinguish between static parts of the captured environment, which correspond to the interior environment, and dynamic parts of the captured environment, which correspond to a moving exterior environment of the vehicle which is visible through a vehicle window. The movement of the data glasses relative to an environment of the vehicle can be determined by use of the captured dynamic parts. The additional consideration of the relative movement between the data glasses and the environment can further reduce the discrepancy between visual perception and vestibular perception.

In one embodiment, the vehicle is configured to differently provide adjustment ranges of vehicle components, for example a positional adjustment range of a front seat, depending on the use of the data glasses. When using data glasses, the distance between the data glasses fitted to the wearer's head and an airbag of the vehicle is reduced, for example, in comparison with the distance between the wearer's head and the airbag of the vehicle on account of the space requirement of the data glasses, as a result of which the triggered airbag can transmit a pulse to the data glasses and indirectly to the wearer's head, which can be associated with a risk of injury to the occupant. This can be prevented by the wearer of data glasses being able to adjust his vehicle seat to a lesser extent in the forward direction than an occupant of the vehicle who is not wearing data glasses. In other words, the adjustment range of a vehicle seat can be reduced in its front region if the occupant sitting on the vehicle seat is wearing data glasses.

In a further embodiment, the data glasses are configured to integrate information relating to objects in an environment of the vehicle into a calculated virtual 3-D scene, for example using imagery. For example, attractions, that is to say points of interest (POI) or products of interest (product placement) can be integrated into the virtual 3-D scene by providers in the environment of the vehicle. In this case, imagery appropriate to the theme of the virtual 3-D scene can be used.

In one example embodiment, the data glasses are configured to play back a two-dimensional moving image stream, for example a movie, on a virtual screen and to display the virtual screen in a calculated virtual 3-D scene which corresponds to the two-dimensional moving images in terms of content. In other words, a theme appropriate to the moving image stream played back on the virtual screen can be selected for the virtual 3-D scene. This makes it possible for the wearer of the data glasses to have a particularly homogeneous experience.

A further subject matter of the disclosure is data glasses for a vehicle which are designed and configured to form, with the vehicle, a system. Such data glasses can be wirelessly connected to the control unit of the vehicle in order to make it possible for an occupant of the vehicle wearing the data glasses to view digital content embedded in a virtual 3-D scene without suffering from motion sickness and in the process to manage with a low bandwidth of the wireless connection.

Also described herein is a method for displaying digital content in a vehicle, for example by use of a system described herein, in which control variables are calculated by a control unit provided in the vehicle from sensor data received from a plurality of sensors provided in the vehicle, the calculated control variables are transmitted from the vehicle to data glasses wirelessly connected to the vehicle, and a virtual 3-D scene integrating the digital content is calculated by the data glasses on the basis of the received control variables. In the method described herein, the virtual 3-D scene is not calculated in the vehicle, but rather by the data glasses. Consequently, there is no need to transmit a large data volume from the vehicle to the data glasses. Rather, a few control variables calculated from the sensor data are sufficient for a virtual 3-D scene consistent with accelerations of the vehicle, the continuous transmission of which control variables accordingly requires a low bandwidth for the wireless connection between the vehicle and the data glasses.

The system is illustrated and described further below on the basis of an embodiment of the system according to the disclosure for viewing digital content by an occupant in a vehicle without suffering from motion sickness.

The system includes a vehicle having a control unit provided in the vehicle and a plurality of sensors which are provided in the vehicle and are connected to the control unit. The system also includes data glasses for displaying a virtual 3-D scene integrating the digital content. The vehicle, for example the sensors provided in the vehicle, and the data glasses have wireless WiFi communication interfaces which are complementary to one another and by which the vehicle and the data glasses are connected to one another.

The control unit is configured to calculate control variables for the data glasses from sensor data received from the sensors as part of preprocessing and to wirelessly transmit the control variables to the data glasses by use of the WiFi communication interface. The control variables include an absolute position, an angle with respect to the horizon, a lateral acceleration and a longitudinal acceleration of the vehicle.

The data glasses are configured to receive the control variables calculated by the control unit, to post-process the control variables and to calculate the virtual 3-D scene on the basis of the received and post-processed control variables. The post-processing of the control variables received at discrete times is used to interpolate a continuous profile of the control variables by use of smoothing.

The system also includes a smartwatch for displaying vehicle or journey parameters, for example a remaining distance to a destination or an available energy reserve. The smartwatch has a wireless WiFi communication interface and is wirelessly connected to the vehicle or to the data glasses. The data glasses are configured to integrate a virtual smartwatch corresponding to the smartwatch into the calculated virtual 3-D scene, with the result that the vehicle parameters or journey parameters displayed by the smartwatch are also visible on the virtual smartwatch.

The data glasses are configured to integrate a visual indication, in particular an indication using imagery, for a wearer of the data glasses, in particular for a driver of the vehicle, into the calculated virtual 3-D scene in order to request the wearer of the data glasses to remove the data glasses. As an indication using imagery, the data glasses display a portal which is virtually passed through by the driver of the vehicle wearing the data glasses.

The data glasses include a camera for capturing an environment of the data glasses and a digital model of an interior environment of the vehicle. They are configured to use the digital model to distinguish between static parts of the captured environment, which correspond to the interior environment, that is to say to the interior of the vehicle, and dynamic parts of the captured environment, which correspond to a relatively moving exterior environment of the vehicle which is visible through a vehicle window.

The vehicle is configured to differently provide a positional adjustment range of a front seat depending on whether or not the occupant sitting on the front seat is wearing data glasses.

The data glasses are also configured to integrate information relating to objects in an environment of the vehicle into the calculated virtual 3-D scene, for example using imagery. For this purpose, locations of particular providers in the environment of the vehicle, special advertising indications or factual tourist information relating to attractions in the environment of the vehicle appropriate to the theme of the virtual 3-D scene are displayed, for example.

The data glasses are configured to play back a movie on a virtual screen integrated into the virtual 3-D scene. In this case, the virtual screen is displayed in a calculated virtual 3-D scene which corresponds, in terms of theme, to the two-dimensional moving images. For example, the virtual 3-D scene may simulate a flight using the Death Star known from the Star Wars movies, whereas an episode of one of the Star Wars movies is played back on the virtual screen.

During operation of the system described herein, control variables are calculated from sensor data by the control unit and are transmitted to the data glasses wirelessly connected to the vehicle. The data glasses calculate a virtual 3-D scene integrating the digital content on the basis of the received control variables.

One advantage of the system described herein is that it is possible for an occupant of a vehicle wearing data glasses to view digital content within a data-intensive VR application matched in terms of theme to the digital content without suffering from motion sickness, without holding a high bandwidth for a wireless connection between the data glasses and the vehicle. As a result, the wearer of the data glasses is provided with a homogeneous and integrated experience of the digital content with simple manageability at the same time. This advantage is intensified further if a plurality of occupants of a vehicle are viewing different digital contents at the same time.

BRIEF DESCRIPTION OF THE DRAWINGS

These and other aspects and advantages will become more apparent and more readily appreciated from the following description of the example embodiments which will be described further with reference to various examples and the associated drawing, in which the single drawing is a schematic illustration of an embodiment of the system described herein.

DETAILED DESCRIPTION

Reference will now be made in detail to examples which are illustrated in the accompanying drawing.

The single drawing schematically shows an embodiment of the system 1000 for viewing digital content in a vehicle without suffering from motion sickness.

In the embodiment illustrated, the system 1000 includes a vehicle 100 having a control unit (controller) 110 and a plurality of sensors 120 connected to the controller, and data glasses 200 which can be wirelessly connected to the controller 110 and are intended to display a virtual 3-D scene integrating the digital content. The vehicle 100 and the data glasses 200 each have wireless communication interfaces 130, 230 which are complementary to one another, for example IR interfaces, Bluetooth interfaces, WiFi interfaces and/or NFC interfaces.

The system 1000 may also include a mobile terminal 300 which can be wirelessly connected to the vehicle 100 and/or to the data glasses 200 and is intended to display vehicle parameters and/or journey parameters.

The data glasses 200 may include at least one optical sensor 220, for example a camera, for capturing an environment of the data glasses 200 and a memory 240 which stores a digital model of an interior environment of the vehicle, and the data glasses 200 may be configured to use the digital model to distinguish between static parts of the captured environment, which correspond to the interior environment, and dynamic parts of the captured environment, which correspond to a moving exterior environment of the vehicle 100 which is visible through a vehicle window. The data glasses 200 include a processor 210 to carry out operations, for example processing and calculating operations, of the data glasses 200.

A description has been provided with reference to embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide* v. DIRECTV, 358 F3d 870, 69 USPQ2d 1865 (Fed. Cir. 2004).

The invention claimed is:

1. A system for viewing digital content in a vehicle, the system comprising:
   a plurality of sensors, and
   a controller of the vehicle, connected to the plurality of sensors, configured to calculate control variables related to a virtual three-dimensional scene (virtual 3-D scene) and a movement of the vehicle from sensor data received from the plurality of sensors, so that the control variables are wirelessly transmittable to other processor to control a calculation of the virtual 3-D scene in real time by the other processor in a manner consistent with a movement of the vehicle, the sensor data being pre-processed by the controller so that the controller calculates from the sensor data fewer control variables than the sensor data, the fewer control variables reducing a volume of data to be transmitted; and
   data glasses to wirelessly communicate with the controller of the vehicle and including the other processor to control wireless connectivity to the controller of the vehicle, the other processor of the data glasses further configured to,
   receive the control variables from the controller of the vehicle,
   calculate a virtual 3-D scene based on the control variables received from the controller of the vehicle, and
   control the data glasses to display the virtual 3-D scene with the digital content integrated in the virtual 3-D scene in the real time in the manner consistent with the movement of the vehicle so as to reduce motion sickness of an occupant of the vehicle wearing the data glasses.

2. The system as claimed in claim 1, wherein
   the vehicle and the data glasses each have at least one wireless communication interface, and
   the at least one wireless communication interface includes at least one of an infrared wireless communication interface, a Bluetooth wireless communication interface, a WiFi wireless communication interface, or a near field communication wireless communication interface.

3. The system as claimed in claim 1, wherein the control variables calculated by the controller include an absolute position, an angle with respect to a horizon, a lateral acceleration, and a longitudinal acceleration of the vehicle.

4. The system as claimed in claim 1, wherein the data glasses are configured to, before calculating the virtual 3-D scene, perform post-processing on the control variables received from the controller by smoothing the control variables.

5. The system as claimed in claim 1, further comprising:
   a mobile terminal, wirelessly connectable to the vehicle and/or to the data glasses, configured to display vehicle parameters and/or journey parameters, and
   wherein the data glasses are configured to integrate a virtual terminal corresponding to the mobile terminal as the digital content into the virtual 3-D scene, such that the vehicle parameters and/or the journey parameters displayed by the mobile terminal are visible on the virtual terminal.

6. The system as claimed in claim 5, wherein,
   the mobile terminal is a smartwatch, and
   the data glasses are configured to integrate a virtual smartwatch corresponding to the smartwatch as the digital content into the virtual 3-D scene, such that the vehicle parameters and/or the journey parameters displayed by the smartwatch are visible on the virtual smartwatch.

7. The system as claimed in claim 1, wherein the data glasses are configured to integrate a visual indication, for a wearer of the data glasses, into the virtual 3-D scene to request the wearer of the data glasses to remove the data glasses.

8. The system as claimed in claim 1, wherein the data glasses are configured to display a portal as a visual indication in the virtual 3-D scene to request a wearer of the data glasses to remove the data glasses.

9. The system as claimed in claim 1, wherein,
the data glasses include:
at least one optical sensor configured to capture an environment of the data glasses, and
a memory to store a digital model of an interior environment of the vehicle, and
the data glasses are configured to use the digital model to distinguish between static parts of the environment captured by the at least one optical sensor, which correspond to the interior environment, and dynamic parts of the environment captured by the at least one optical sensor, which correspond to an exterior environment of the vehicle visible through a window of the vehicle, so as to integrate into the virtual 3-D scene a visual indication as the digital content based on the static parts of the environment and the dynamic parts of the environment.

10. The system as claimed in claim 1, wherein the vehicle is configured to adjust a position of a seat and an airbag of the vehicle when the occupant wearing the data glasses is seated in the seat, to increase a distance between the seat and the airbag.

11. The system as claimed in claim 1, wherein the data glasses are configured to:
integrate information relating to objects in an environment of the vehicle into the virtual 3-D scene, and/or
play back a two-dimensional moving image, on a virtual screen integrated into the virtual 3-D scene, the virtual screen being displayed in the virtual 3-D scene which corresponds to the two-dimensional moving image in terms of content.

12. The system as claimed in claim 1, wherein
a frequency at which the controller calculates the control variables from the sensor data received from the plurality of sensors is lower than a frequency at which the controller receives the sensor data from the plurality of sensors.

13. Data glasses for a vehicle, comprising:
a communication interface configured to wirelessly connect to a controller of a vehicle to receive control variables related to a virtual three-dimensional scene (virtual 3-D scene) and movement of the vehicle calculated by the controller of the vehicle based on sensor data received by the controller of the vehicle from a plurality of sensors of the vehicle, so that the virtual 3-D scene is calculatable in real time based on the control variables in a manner consistent with a movement of the vehicle, the sensor data being pre-processed by the controller so that the controller calculates from the sensor data fewer control variables than the sensor data, the fewer control variables reducing to reduce a volume of data to be transmitted and received by the communication interface; and
a processor configured to calculate a virtual 3-D scene based on the control variables received from the controller of the vehicle, and
control the data glasses to display the virtual 3-D scene with digital content integrated in the virtual 3-D scene in the real time in the manner consistent with the movement of the vehicle so as to reduce motion sickness of an occupant of the vehicle wearing the data glasses.

14. The data glasses as claimed in claim 13, wherein the control variables calculated by the controller include an absolute position, an angle with respect to a horizon, a lateral acceleration, and a longitudinal acceleration of the vehicle.

15. The data glasses as claimed in claim 13, wherein the processor is configured to, before calculating the virtual 3-D scene, perform post-processing on the control variables received from the controller by smoothing the control variables.

16. The data glasses as claimed in claim 13, wherein
the communication interface is configured to wirelessly connect to a mobile terminal which is configured to display vehicle parameters and/or journey parameters of the vehicle, and
the processor is configured to integrate a virtual terminal corresponding to the mobile terminal as the digital content into the virtual 3-D scene, such that the vehicle parameters and/or the journey parameters displayed by the mobile terminal are visible on the virtual terminal.

17. The data glasses as claimed in claim 13, further comprising:
at least one optical sensor configured to capture an environment of the data glasses; and
a memory to store a digital model of an interior environment of the vehicle,
wherein
the processor is configured to use the digital model to distinguish between static parts of the environment captured by the at least one optical sensor, which correspond to the interior environment, and dynamic parts of the environment captured by the at least one optical sensor, which correspond to an exterior environment of the vehicle, so as to integrate into the virtual 3-D scene a visual indication as the digital content based on the static parts of the environment and the dynamic parts of the environment.

18. The data glasses as claimed in claim 13, wherein the processor is configured to:
integrate information relating to objects in an environment of the vehicle into the virtual 3-D scene, and/or
play back a two-dimensional moving image, on a virtual screen integrated into the virtual 3-D scene, the virtual screen being displayed in the virtual 3-D scene which corresponds to the two-dimensional moving image as the digital content.

19. A method of displaying digital content in a vehicle, the method comprising:
obtaining sensor data, by a plurality of sensors of the vehicle, relating to movement of the vehicle;
calculating, by a controller of the vehicle, control variables related to a virtual three-dimensional scene (virtual 3-D scene) and the movement of the vehicle, from the sensor data obtained by the plurality of sensors, so that the virtual 3-D scene is calculatable in real time based on the control variables in a manner consistent with a movement of the vehicle, the sensor data being pre-processed by the controller so that the controller calculates from the sensor data fewer control variables than the sensor data, the fewer control variables reducing a volume to be transmitted;

wirelessly transmitting, by the controller of the vehicle, the control variables to a processor of data glasses wirelessly connected to the controller of the vehicle;

calculating, by the processor of the data glasses, a virtual 3-D scene based on the control variables received from the controller of the vehicle; and displaying, by the data glasses, the virtual 3-D scene with the digital content integrated in the virtual 3-D scene in the real time in the manner consistent with the movement of the vehicle so as to reduce motion sickness of an occupant of the vehicle wearing the data glasses.

20. The method as claimed in claim 19, wherein the control variables calculated by the controller include an absolute position, an angle with respect to a horizon, a lateral acceleration, and a longitudinal acceleration of the vehicle.

* * * * *

UNITED STATES PATENT AND TRADEMARK OFFICE
CERTIFICATE OF CORRECTION

PATENT NO. : 12,062,232 B2  
APPLICATION NO. : 16/652639  
DATED : August 13, 2024  
INVENTOR(S) : Daniel Profendiner Page 1 of 1

It is certified that error appears in the above-identified patent and that said Letters Patent is hereby corrected as shown below:

In the Claims

Column 9, Lines 64-65:
In Claim 13, after "reducing" delete "to reduce"

Column 11, Line 2:
In Claim 19, after "volume" insert --of data--.

Signed and Sealed this
Twenty-second Day of October, 2024

Katherine Kelly Vidal
*Director of the United States Patent and Trademark Office*